(12) United States Patent
Xiao

(10) Patent No.: US 11,197,986 B2
(45) Date of Patent: Dec. 14, 2021

(54) DEVICES FOR APPLYING COLOURED LIQUID TO SKIN

(71) Applicant: Long Xiao, Scarborough (CA)

(72) Inventor: Long Xiao, Scarborough (CA)

( * ) Notice: Subject to any disclaimer, the term of this patent is extended or adjusted under 35 U.S.C. 154(b) by 51 days.

(21) Appl. No.: 16/543,913

(22) Filed: Aug. 19, 2019

(65) Prior Publication Data

US 2019/0366069 A1 Dec. 5, 2019

Related U.S. Application Data

(63) Continuation-in-part of application No. 15/691,125, filed on Aug. 30, 2017, now Pat. No. 10,806,915.

(30) Foreign Application Priority Data

Aug. 24, 2018 (CN) .......................... 201810976051.6

(51) Int. Cl.
 *A61M 37/00* (2006.01)
(52) U.S. Cl.
 CPC ............................... *A61M 37/0076* (2013.01)
(58) Field of Classification Search
 CPC .............. A61M 5/3202; A61M 5/3234; A61M 5/3287; A61M 2205/0216; A61M 2205/197
 USPC ........................................... 81/9.22; 606/185
 See application file for complete search history.

(56) References Cited

U.S. PATENT DOCUMENTS

| | | | |
|---|---|---|---|
| 6,345,553 B1 | 2/2002 | Adler et al. | |
| 6,505,530 B2 | 1/2003 | Adler et al. | |
| 8,029,527 B2 | 10/2011 | Lisec | |
| 2009/0183602 A1 | 7/2009 | Crockett | |
| 2010/0206138 A1 | 8/2010 | Clark | |
| 2011/0048174 A1* | 3/2011 | Lin | A61M 37/0084 81/9.22 |
| 2012/0041374 A1 | 2/2012 | Lee | |

(Continued)

FOREIGN PATENT DOCUMENTS

| | | |
|---|---|---|
| CA | 2917187 A1 | 1/2015 |
| CN | 2356645 Y | 1/2000 |
| CN | 201595866 U | 10/2010 |

(Continued)

OTHER PUBLICATIONS

Extended European Search Report dated Feb. 4, 2019 in related EP Patent Application No. 18191616.4.

*Primary Examiner* — David B. Thomas
*Assistant Examiner* — Thomas Raymond Rodgers

(57) ABSTRACT

A handle for an applicator of coloured liquid to skin comprises a removable needle module and a needle actuator. The needle module comprises a needle. The handle comprises a handle body having top and bottom portions. The top portion is engagable with the needle actuator and has a top opening for receiving a drive shaft of the needle actuator. The bottom portion is removably engagable with the needle module and has a bottom opening for receiving a needle shaft of the needle. A reciprocally movable interface sealingly engages an internal surface of the handle body. The interface separates the bottom opening from the top opening so as to prevent fluid communication from the bottom opening to the top opening, and is configured to abut the drive shaft and the needle shaft during use to allow the drive shaft to indirectly drive the needle shaft.

17 Claims, 15 Drawing Sheets

(56) References Cited

U.S. PATENT DOCUMENTS

2015/0352346 A1 12/2015 Webb
2016/0184572 A1 6/2016 Xiao

FOREIGN PATENT DOCUMENTS

| CN | 106902452 A | 6/2017 |
|----|-------------|--------|
| EP | 2420265 A2 | 2/2012 |
| EP | 2896427 A1 | 7/2015 |

* cited by examiner

DEVICES FOR APPLYING COLOURED LIQUID TO SKIN

CROSS-REFERENCE TO RELATED APPLICATIONS

This application is a continuation-in-part application of U.S. patent application Ser. No. 15/691,125, filed Aug. 30, 2017, entitled "Devices for Applying Coloured Liquid to Skin", the entire contents of which are incorporated herein by reference.

This application also claims the benefit of, and priority from, Chinese Invention Patent Application No. 201810976051.6, filed Aug. 24, 2018, the entire contents of which are incorporated herein by reference.

FIELD

The present invention relates generally to devices for applying coloured liquid onto skin, particularly to devices such as tattooing devices or devices for applying permanent make-up, needle handles thereof, or kits therefor.

BACKGROUND

A tattooing device typically includes a needle for applying ink to skin, a base with a needle actuator, and a needle handle that connects the needle to the base and can be conveniently held in a hand of an operator for manipulating the needle during use. For safety reasons, the needle should be sterilized before use and replaced after each use. It is thus convenient to use replaceable needle modules, which can be easily detached or connected to the needle handle so that the needle can be easily replaced. It may also be necessary to sterilize the needle handle before and after each use to prevent cross-contamination.

Examples of such devices are described in US 20160184572 published Jun. 30, 2016, and CN 201595866U issued Oct. 6, 2010, both by the present inventor.

The needle handle may also be detachable from the base and be conveniently replaceable. Single-use needle handles may be used.

Devices or applicators for applying permanent mark-up may have a similar construction, with a base, a replaceable handle, and a replaceable needle module.

It is desirable to improve such and other devices for applying coloured liquid to skin.

SUMMARY

An aspect of the present disclosure relates to a handle for an applicator of a coloured liquid to skin, wherein the applicator comprises a needle and a needle actuator, the handle comprising a tubular body having a top end and a bottom end and defining an inner channel extending from the top end towards the bottom end, the top end configured to engage the needle actuator or a handle connector for connecting the tubular body to the needle actuator, the bottom end configured to engage a needle module comprising the needle; an inner tubing extending inside the channel from the bottom end towards the top end, and having an open top; a seal sealing the open top of the inner tubing, the seal comprising a reciprocally movable interface, the top surface of the interface positioned to abut a drive shaft of the needle actuator and the bottom surface of the interface positioned to abut a needle shaft of the needle such that the drive shaft and the needle shaft interact through the interface. The inner tubing may be a tubular stub and the seal may comprise a sealing cap capping the open top of the tubular stub, and the sealing cap may comprise a base portion engaging the tubular stub, a top portion above the open top, an extendable portion (such as a bellows portion or a portion formed of a resilient material) connecting the base portion and the top portion such that the top portion functions as the interface. The open top of the inner tubing may comprise an O-ring groove, and the seal may comprise an O-ring seated in the groove and a piston plug through the O-ring for functioning as the interface, where the O-ring sealingly engages the groove and the piston plug. The tubular body may be generally cylindrical. The tubular body may be formed of a plastic. The sealing cap may be formed of a silicone or a rubber. The inner tubing may be generally cylindrical. The handle may comprise the handle connector. The tubular body may have a threaded channel section for threadedly engaging the handle connector. The handle may comprise a constriction ring clamping the base portion of the sealing cap to the tubular stub.

Another aspect of the disclosure relates to a handle for an applicator of a coloured liquid to skin, wherein the applicator comprises a needle and a needle actuator. The handle comprises a handle body having a top portion and a bottom portion; the top portion having an opening for receiving a drive shaft of the needle actuator; the bottom portion comprising an inner tubing, the inner tubing comprising an open bottom for receiving a needle shaft of the needle, a closed top, and an extendable section (such as a bellows section or a section formed of a resilient material) below the closed top so that the closed top is reciprocally moveable.

A further aspect of the disclosure relates to a handle for an applicator of a coloured liquid to skin, wherein the applicator comprises a needle and a needle actuator. The handle comprises a handle body having a top portion and a bottom portion, the top portion engagable with the needle actuator and having a top opening for receiving a drive shaft of the needle actuator, the bottom portion engagable with a needle module comprising the needle and having a bottom opening for receiving a needle shaft of the needle; and a reciprocally movable interface sealingly engaging an internal surface of the handle body, the interface separating the bottom opening from the top opening so as to prevent fluid communication from the bottom opening to the top opening, and configured to abut the drive shaft and the needle shaft during use to allow the drive shaft to indirectly drive the needle shaft. The interface may be in sliding engagement with the internal surface of the handle body. The top opening and bottom opening may be sized and shaped to form a shoulder, and the interface may comprise a sealing cap affixed to the shoulder. The interface may comprise a fixed base portion, a movable top portion, and an extendable portion (such as a bellows portion or a portion formed of a resilient material) connecting the base portion and the top portion. The interface may be formed of a silicone or a rubber. The position of the interface in the handle may be axially adjustable for adjusting an exposed length of the needle in the needle module when the needle module is engaged with the handle.

In another aspect, there is provided a tattooing device comprising a base and a handle as described herein. The base comprises a needle actuator. The top end of the handle is connected to the base. A needle module may be attached to the handle, and may be engaged with the bottom end of the handle.

A further aspect of the disclosure relates to a kit comprising a handle as described herein and one or more needle modules. The handle and the one or more needle modules may be sterilized and sealed in a sterilized package.

Another aspect of the present disclosure relates to a package comprising a handle as described herein, wherein the handle has been sterilized; and a sterilized packaging enclosing the handle therein for keeping the handle in a sterilized condition.

Other aspects, features, and embodiments of the present disclosure will become apparent to those of ordinary skill in the art upon review of the following description of specific embodiments in conjunction with the accompanying figures.

BRIEF DESCRIPTION OF THE DRAWINGS

In the figures, which illustrate, by way of example only, embodiments of the present disclosure.

DETAILED DESCRIPTION

The present disclosure relates to devices and applicators for applying a liquid, particularly colored liquid, to skin. The applicators include tattooing devices or devices for applying make-up, particularly permanent make-up, such as for applying make-ups to eyebrow or mouth, or applying eyeliners, or the like. The example embodiments described below use tattooing devices to illustrate features of the disclosed applicators and devices.

An embodiment of the present disclosure relates to a tattooing device as illustrated in FIGS. 1 to 6.

Figure 1:
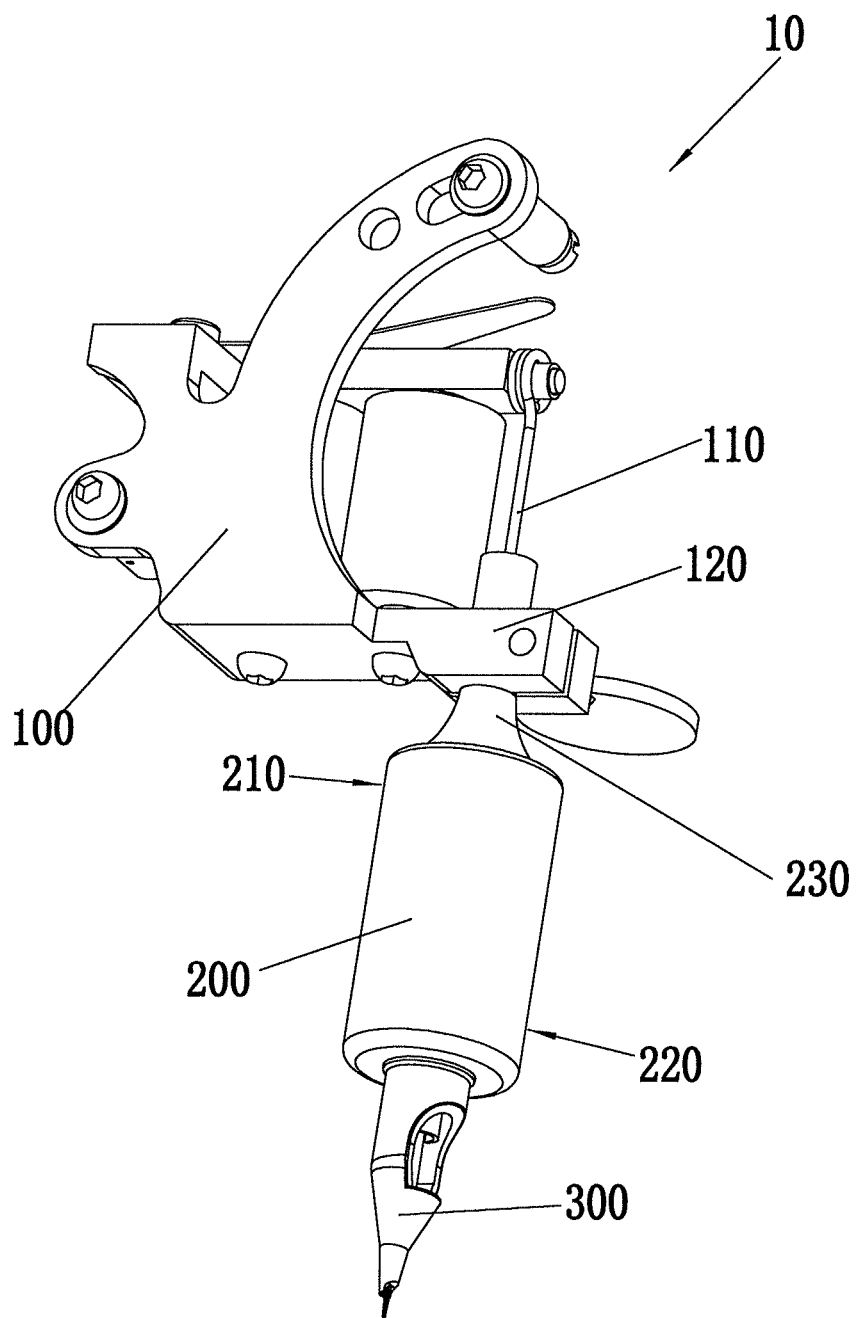
FIG. 1 is a perspective view of a tattooing device, illustrative of an embodiment of the present disclosure.
Figure 2:
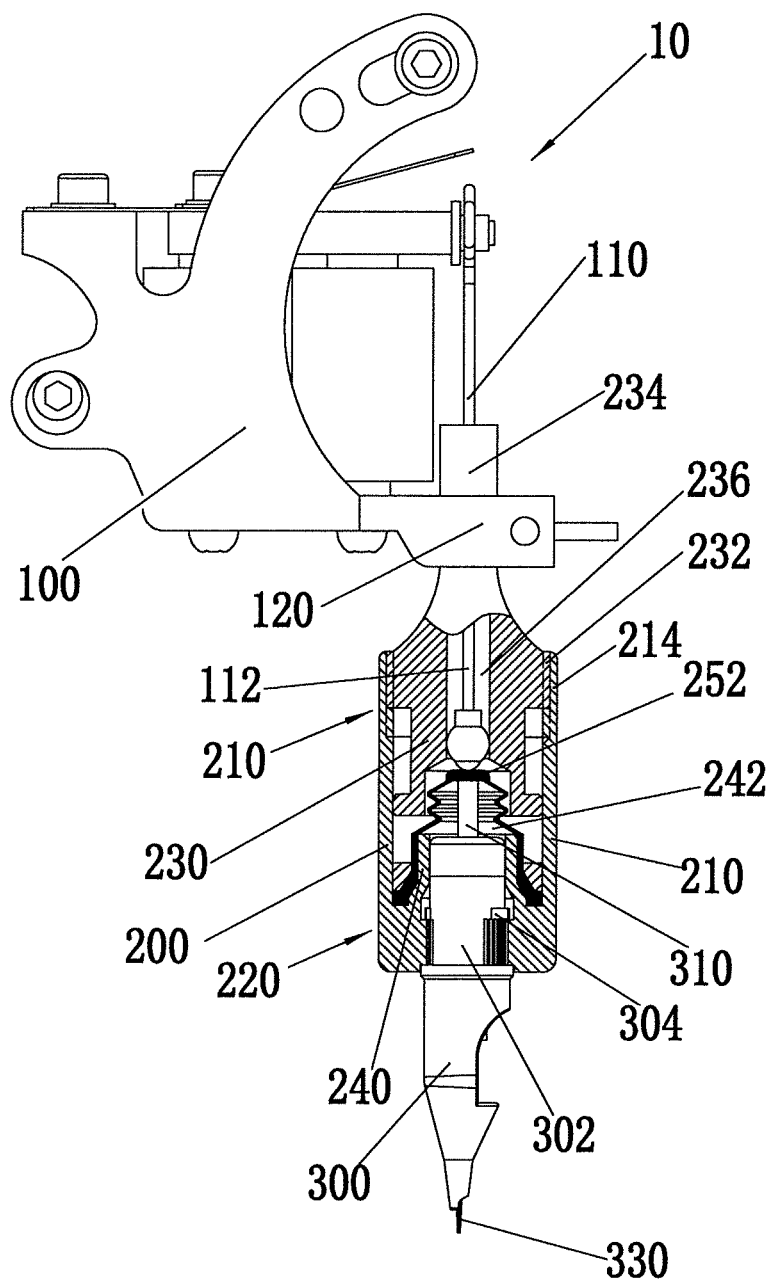
FIG. 2 is a side partial elevation and partial cross-sectional view of the tattooing device of FIG. 1.
Figure 3:
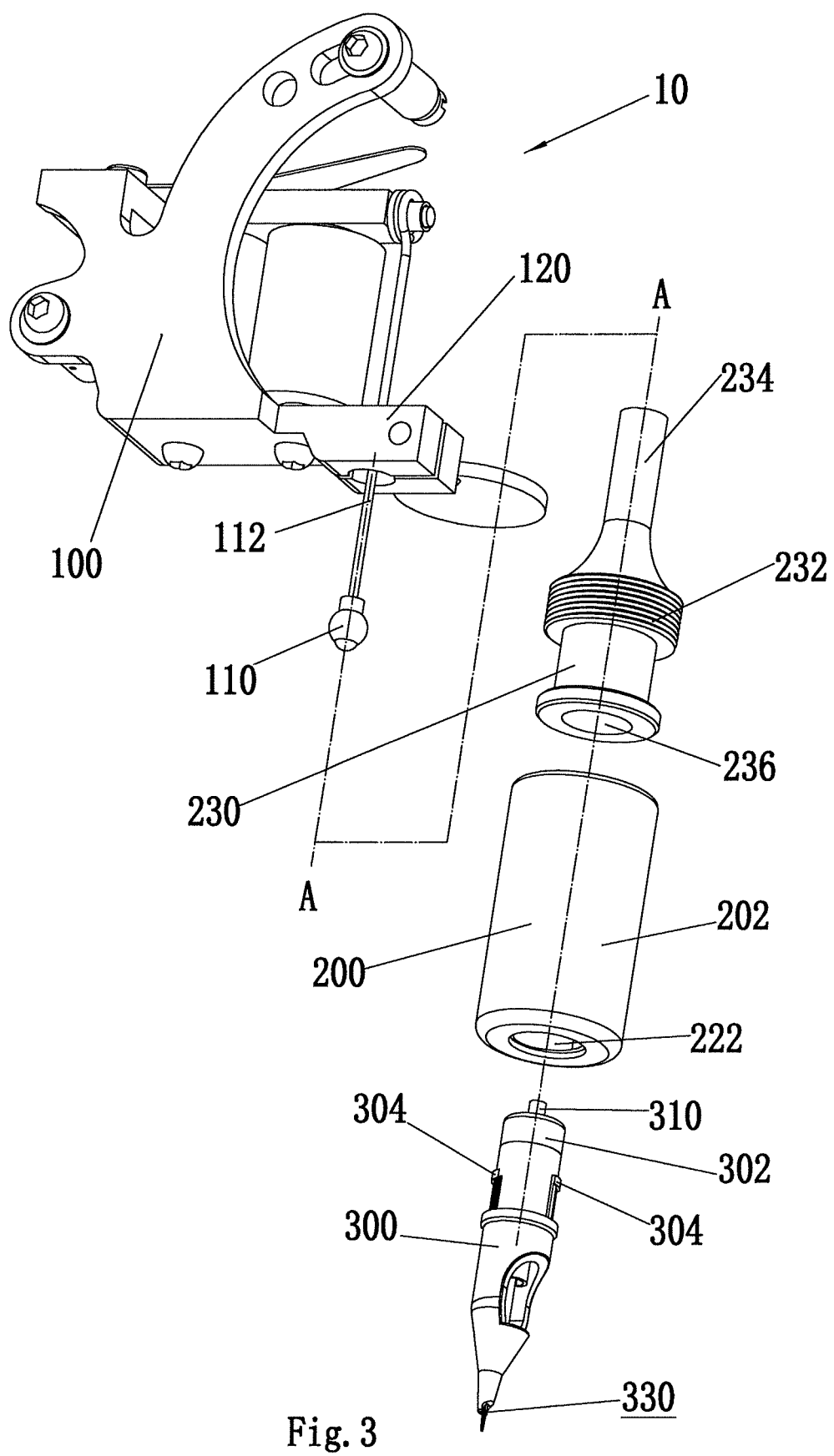
FIG. 3 is an exploded perspective view of the tattooing device of FIG. 1.

As shown in FIGS. 1 to 3, a tattooing device 10, including a base 100, a handle 200, and a needle module 300.

The base 100 includes a needle actuator 110 having a drive shaft 112, and a clamp 120.

The handle 200 has a generally tubular shape, which may be cylindrical as illustrated in the figures. A tubular shape has an inner opening or channel but is not necessarily cylindrical or has a circular cross-section, and does not have to have equal cross-sectional size along its length. The tubular shape may include an outer profile that is a ball-shape and an inner channel. In further embodiments, the tubular shape may include a vase shape or a bell shape.

A connector 230 is provided and configured to detachably connect the handle 200 to the base 100. The top end 210 of the handle 200 is configured for detachable coupling with the connector 230, such as by a threaded coupling mechanism. The top end 234 of connector 230 is configured to engage the base 100. As depicted, the top end 234 of connector 230 has cylindrical shape and can be clamped by clamp 120. The connector 230 has a through opening 236 that allows the drive shaft 112 to pass through. For clarity, it is noted that for the purpose of this disclosure, the connector 230 is considered a separate part, not necessarily a component of the handle 200.

The clamp 120 may be an adjustable clamp so that the clamping force or pressure can be adjusted. The relative axial position of the connector 230, and hence the handle 200, relative to drive shaft 112 of base 100, may be adjusted when the clamp is slightly loosened, and can be secured by tightening the clamp 120.

The bottom end 220 of handle 200 is configured to receive and removably engage the needle module 300.

The needle module 300 has a top end 302 configured to be mounted at the bottom end 220 of the handle 200. A needle 330 is housed in the needle module 300. The needle module 300 may be disposed after a single use. The needle 330 is retractable, and the sharp tip of the needle 330 can be hidden in the needle module 300 when not in use. The needle 330 is reciprocally movable within the needle module 300, and the needle module 300 includes a biasing mechanism (not shown) that biases the needle 330 upwards as depicted, as can be appreciated by those skilled in the art.

When the base 100, handle 200 and needle module 300 are assembled for operation, the needle 330 can be actuated by the actuator 110. In particular, when the drive shaft 112 extends downwards as depicted in the figures, the needle 330 is pushed downwards. When the drive shaft 112 retracts upwards, the needle 330 also retracts upwards due to the internal biasing mechanism. As a result, the actuator 110 and the internal biasing mechanism can drive the needle 330 to move reciprocally up and down for puncturing the skin of a subject.

An ink or other coloured fluid may be applied to the puncture skin using the needle 330, as can be appreciated by those skilled in the art. The handle 200 is sized and shaped to be conveniently held in a hand of an operator (e.g. tattooist) to apply the ink to the skin.

The construction and operation of the base 100, the driving mechanism 110, and the needle module 300 are known in the art and can be similar to, for example, the corresponding parts described in US 20160184572, US 20090183602, EP2896427 or CN 201595866U, the entire contents of each of which are incorporated herein by reference. As such, these parts and their operation are not described in detail herein. It is generally noted that common tattoo machines include coil tattoo machines and rotatory tattoo machines. A coil tattoo machine uses electromagnetic coils to move the drive shaft (or an armature bar) up and down. A rotatory tattoo machine is powered by a regulated motor. A tattoo machine may be powered by electricity or a pneumatic fluid (such as compressed air).

The handle 200, however, is constructed differently from the needle handle described in US 20160184572 and CN 201595866U, and in other known tattooing devices with a replaceable needle module and needle handle, as will be further discussed below.

Figure 4:
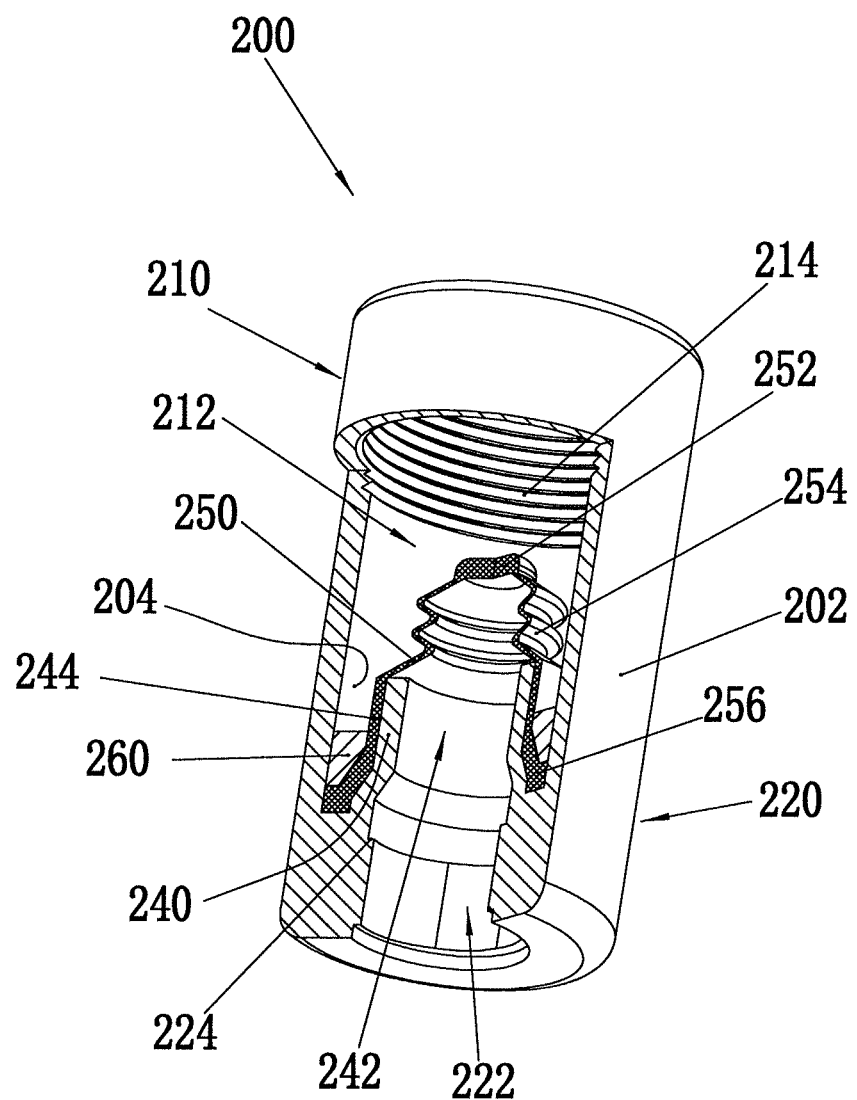
FIG. 4 is partially-cut perspective sectional view of the handle of the tattooing device of FIG. 1.
Figure 5:
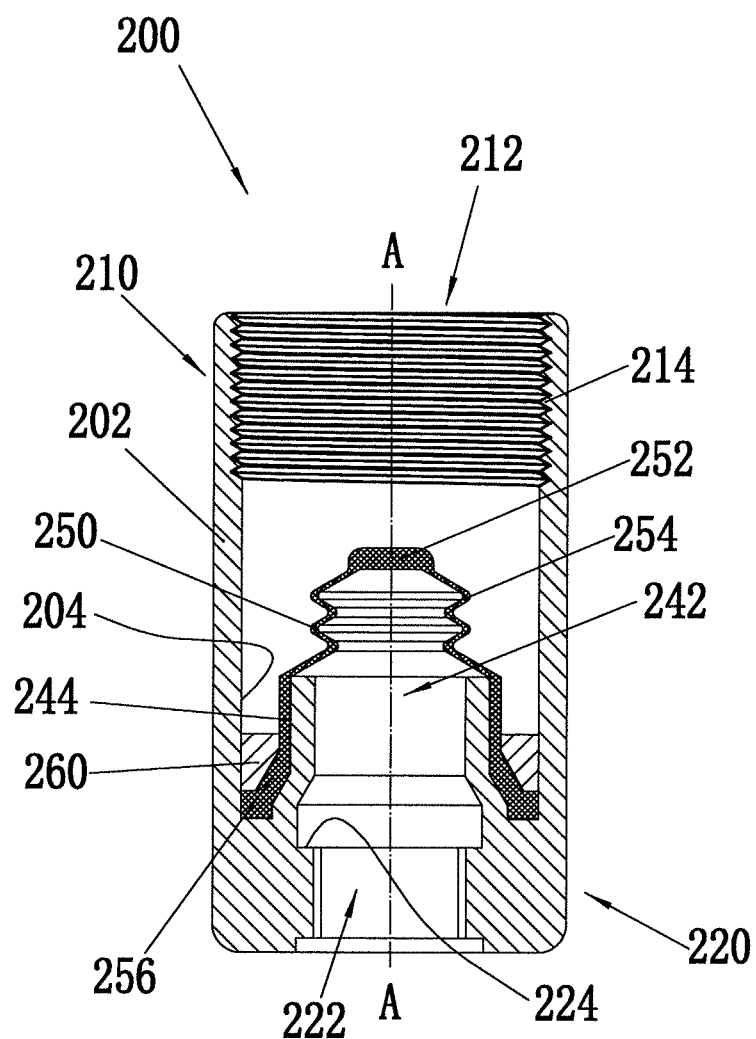
FIG. 5 is a side cross-sectional view of the handle of FIG. 4.
Figure 6:
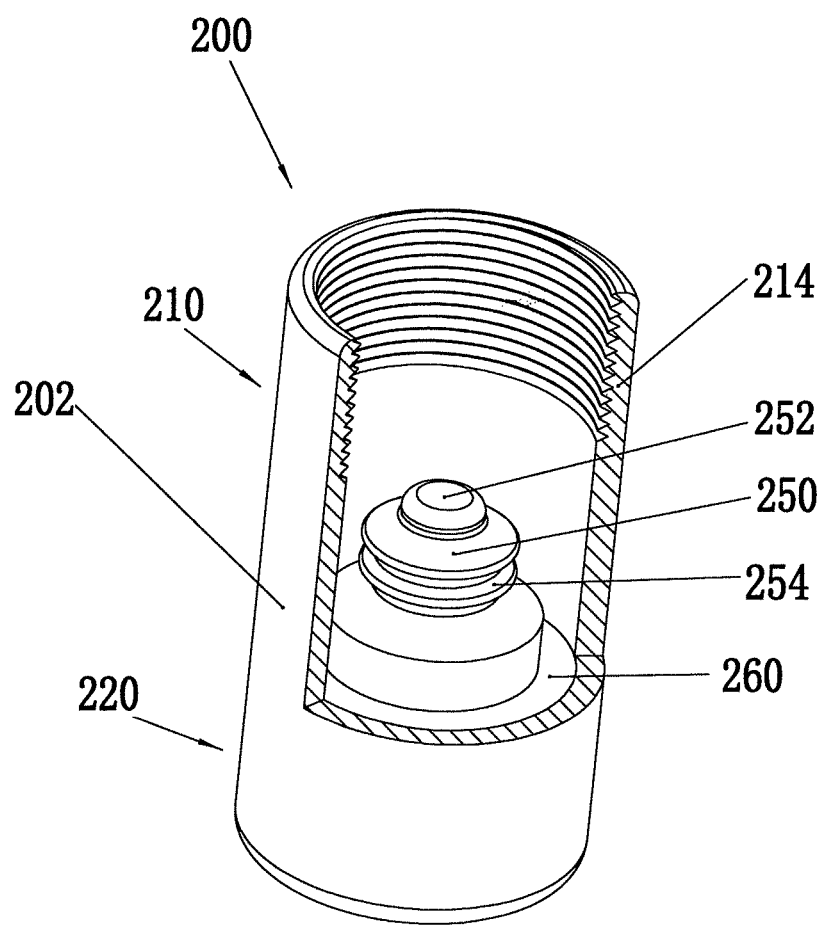
FIG. 6 is a partially-cut perspective view of the handle of FIG. 4.

As illustrated in FIG. 2, and in FIGS. 4, 5 and 6, the handle 200 includes a tubular wall 202, which defines a through channel 212 that allows the actuator 110 to actuate the needle 330.

For example, as illustrated, the actuator 110 may include a drive shaft 112 that extends into the top portion of the channel 212 of the handle 200, so that the drive shaft 112 can act on the needle shaft 310 of the needle 330. The top end 210 of the wall 202 may be provided with a threaded portion 214 and sized to receive a threaded end 232 of the connector 230.

The bottom end of the channel 212 has an opening 222 for receiving the top end 302 of the needle module 300. The bottom end 220 of the handle 200 including the opening 222 and the top end 302 of the needle module are configured to couple and lock the needle module in place when assembled. Any suitable coupling and locking mechanism may be used for this purpose, which is a concern for this disclosure. As illustrated in the figures, the bottom end 220 of the handle may have a bayonet socket (e.g. in the form of a stepped shoulder) 224 and the top end 302 of the needle module 300 may include one or more matching bayonets 304 for engaging and locking the needle module in place once received in the handle 200.

At an intermediate section of the channel 212, an inner tubular stub 240 is provided which extends upwards from the wall 202. The tubular stub 240 has an inner opening 242 sized to allow a top end 302 of the needle 330 to pass therethrough. The outer surface 244 of the tubular stub 240 is spaced from the inner surface 204 of the tubular wall 202. The tubular stub 240 may be cylindrical and may be concentric with the tubular wall 202.

A resilient sealing cap 250 covers the opening 242 over the tubular stub 240 and is frictionally engaged with the outer surface 244 of the tubular stub 240. The sealing cap 250 has a cap top 252 (top portion), a bellows portion 254, and a base portion 256. The cap top 252 is above the open top of the tubular stub 240. The bellows portion 254 connects the base portion 256 and the cap top 252. The base portion 256 engages the tubular stub 240 and the wall 202. The sealing cap 250 may be secured in place by friction, and may be further secured by a constriction ring 260, which is sized and shaped to tightly engage the outer surface of the cap 250 and the inner surface 204 of the tubular wall 202.

The sealing cap 250 may be made of a suitable resilient material such as silicone, which is flexible to allow reciprocal movement of the cap top 252 in the axial direction of the channel 212 (indicated by axis A in FIG. 5). The resilient material may also include a rubber, an elastic polymer or other similar materials. For example, nitrile butadiene rubber (NBR) or a latex material may be used in some embodiments. The cap 250 may also be formed of a soft and flexible material that is not necessarily resilient. In some embodiments, the cap 250 may include a corrugated neck or a bellows section 254, as illustrated in FIGS. 2, 4, 5 and 6, for increasing the movable distance of the cap top 252.

The cap 250 seals and isolates the bottom portion of the channel 212 from the top portion of the channel 212, and allows the drive shaft 112 and the needle 330 to interact through the cap 250. The cap top 252 thus functions as an interface between the drive shaft 112 and the needle shaft 310.

Initially, both the drive shaft 112 and the needle 330 are in a retracted position and abut against the upper surface and the bottom surface of the cap top 252 respectively, as illustrated in FIG. 2. As can be appreciated, during operation of the tattooing device, the actuator 110 is energized to cause reciprocal movement of the drive shaft 112 along the axis A. During a downward movement portion of a reciprocal cycle, the drive shaft 112 extends and pushes the needle 330 downward through the cap top 252. The drive shaft 112 then retracts upwards, and will not act on the needle during retraction, or the upward movement portion of the cycle. However, a recoil or elastic mechanism (not shown) is provided in the needle module 300, which will pull the extended needle 330 back up and return the needle 330 to its retracted position. This cycle is then repeated.

As can be appreciated, during use, ink and a bodily fluid may enter the opening in the bottom portion 220 of the handle 200. Conveniently, the cap 250 fluidly isolates the bottom portion 220 of the handle 200 from the top portion 210 of the handle 200, thus preventing contamination of the drive shaft 112 and the connector 230 by the ink or bodily fluid.

It is possible that the operator only need to touch the handle 200 and do not need to touch the handle connector 230 during operation of the tattooing device. The needle module 300 also will not directly contact the handle connector 230 or actuator 110 (drive shaft 112). Any ink or bodily fluid that may get in contact with the needle 330 and may get into the bottom portion of the handle 200 will also be isolated from the handle connector 230 and the actuator 110, by the sealing cap 250.

After use, the needle module 300 may be removed first. The handle 200 may be next removed. The needle module 300 and handle 200 may then be disposed. The operator can clean her hands at this time before touching other parts of the tattooing device 10.

As a result, the handle body portion including the handle wall 202 and the cap 250, and the needle module 300 may be disposable and discarded after a single use, but the handle connector 230 and the base 100 may be used repeatedly.

Consequently, the drive shaft 112 and handle connector 230 may be made of a durable and rigid material. For example, the rigid material may be stainless steel or aluminium alloy. In contrast, the handle wall 202 and the cap 250 may be made of a less durable material. For example, the handle wall 202 may be formed of a suitable plastic material, and the cap 250 may be formed of a silicone material. When the handle 200 is disposable and for single operation, it may be made of a low cost material. Further, before and after each use, the requirement for sterilizing or sanitizing the drive shaft 112 or handle connector 230 is reduced. Known measures can also be taken to keep the disposable handles and needle modules in sterilized or sanitized conditions before use so that a sterilization or sanitization treatment of these parts before each use is not necessary.

An embodiment of the present disclosure also relates to the handle 200, without the handle connector 230. The handle 200 may be manufactured and supplied separately from the base 100 and the handle connector 230. In some embodiments, the handle 200 may be supplied with a needle module such as needle module 300. In some embodiments, the handle 200 may be supplied without any accompanying needle modules.

An embodiment of the present disclosure relates to a package, which includes the handle 200, and optionally the handle connector 230 or one or more of the needle modules 300. The package may include a sterilized or sanitized packaging enclosing the component parts which are pre-sterilized or pre-sanitized before packaging. When multiple needle modules are provided, the needle modules may include needles of different sizes.

The package may also include instructions for matching tattooing devices or machines, and instructions for mounting or installing the handle 200 and needle module on the tattooing device or machine. The package may indicate that the components are single-use disposable components and provide instructions on how to dispose these parts after use. The package may also include markings or indicia to indicate that the content, such as the handle, has been sterilized, or that the package is a sterilized package, and indicate an expiry date or "best before" date.

The handle may be used directly after opening the packaging without further cleaning, sanitization, or sterilization, and can be disposed of after a single use without cleaning or any other treatment.

For clarity, it is noted that "single use" may refer to use of a needle or handle for one complete operation on a single individual subject. During this operation, different needles may be used with the same handle, or different handles, to apply different colours. For example, it may be typical to use two to five different needles during a single operation on a subject, depending on the complexity of the design to be applied.

In a further embodiment, the handle 200 may be supplied with the handle connector 230. In this case, the handle connector 230 may also be disposable after one or several uses and may be formed of a less durable material, such as a plastic material, instead of a metal material.

As can be appreciated, in this case, the handle and handle connector may be integrated into a single component, and a threaded or other coupling mechanism between them may not be needed.

A handle with an inner sealing cap as disclosed herein is also more convenient to use than a handle that requires an external cover or barrier for preventing contamination by ink or a bodily fluid.

As can be appreciated by those skilled in the art, a similarly constructed handle can also be used in an applicator for applying other colored fluid materials to skin, such as applicators for applying make-ups or other cosmetic materials to skin. The applied materials may include skin care products or dermatology drugs.

Figure 7A:
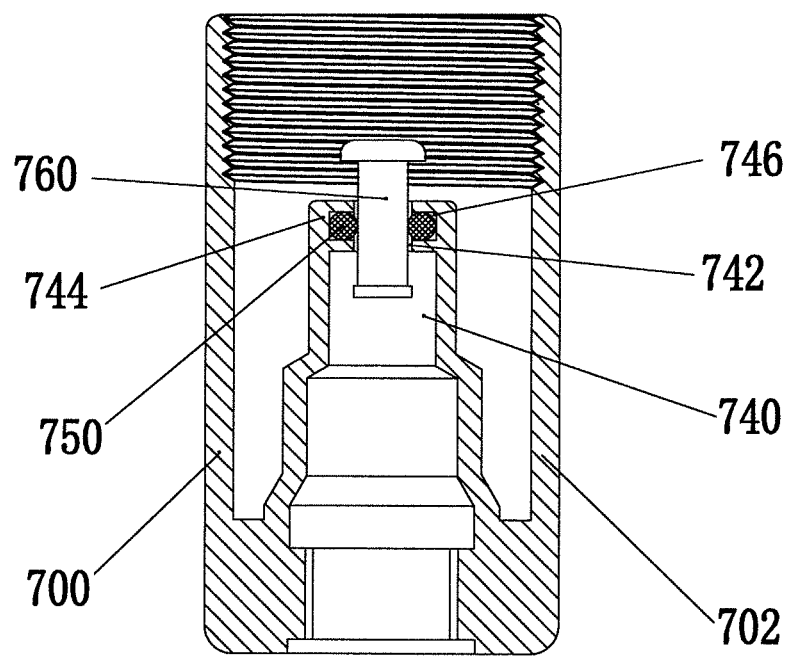
FIG. 7A is a side cross-sectional view of another handle, illustrative of an embodiment of the present disclosure.

FIG. 7A illustrates an alternative embodiment of the handle, handle 700, which includes a sealing O-ring 750 and sealing plug piston 760, instead of a sealing cap.

Figure 7B:
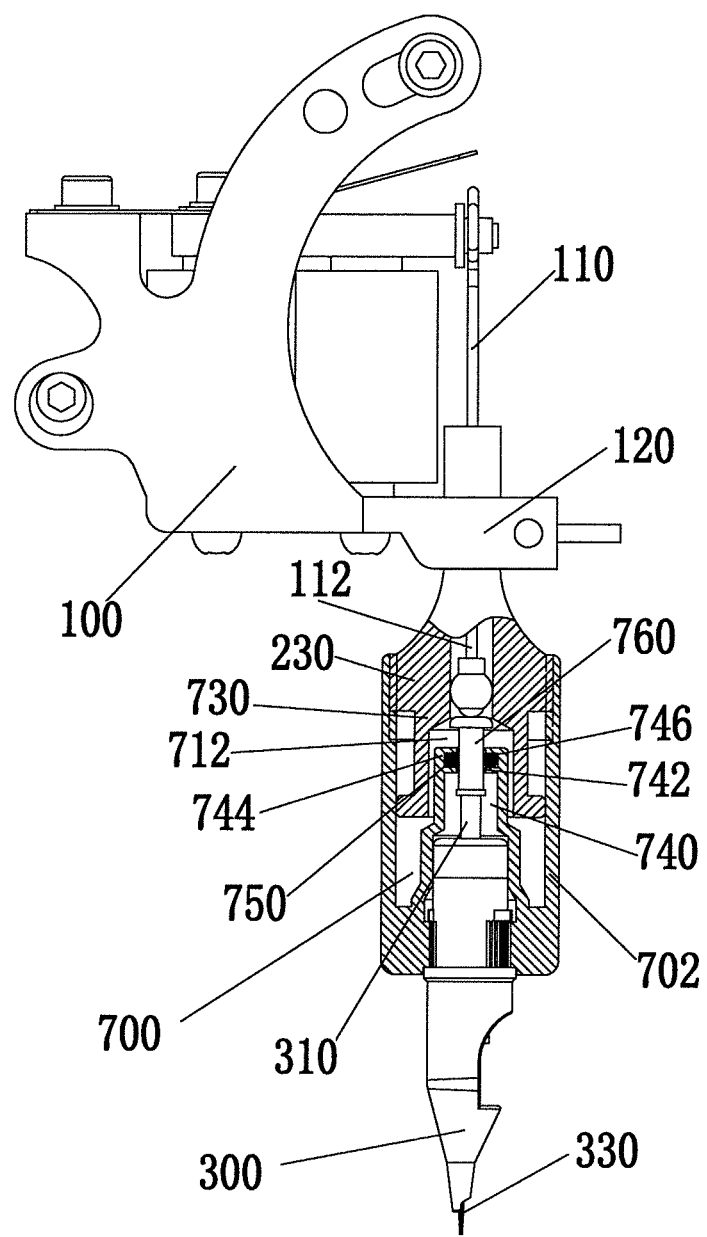
FIG. 7B is a side partial elevation and partial cross-sectional view of an alternative tattooing device including the handle of FIG. 7A.

Similar to the handle 200, the handle 700 includes a tubular wall 702, which defines a through channel 712, and has top and bottom ends configured to engage the handle connector 730 and the needle module 300 respectively. A tattooing device assembled from the handle 700 and the handle connector 730, the base 100 and needle module 300 are illustrated in FIG. 7B. The base 100 and needle module 300 are as described with references to FIGS. 1-6 above.

The intermediate section of the handle 700, however, is constructed differently from that of handle 200. Specifically, instead of a stub, an inner tubular chamber 740 is provided in handle 700. The tubular chamber 740 has an opening 742 at the upper end 744. The opening 742 has a recessed groove 746 for seating a sealing O-ring 750. A piston plug 760 passes through the opening 742 and O-ring 750 for transferring the driving force from the drive shaft 112 to the needle shaft 310. The O-ring 750 sealingly engages both the groove 746 and piston plug 760 to prevent fluid communication through the opening 742 of the chamber 740.

As a result, the lower portion of the handle 700 and the needle module 300 are isolated from the upper portion of the handle 700 and the handle connector 730 and the actuator 110 or the base 100. The O-ring 750 and piston plug 760 thus provide a similar functionality as the sealing cap 250.

The O-ring 750 may be made of a suitable resilient material such as rubber.

The plug 760 may be made of a suitable rigid material for a piston to, transfer mechanical force. The plug 760 has cylindrical central portion so that it can slide in the O-ring 750 while maintaining a fluid seal. The plug 760 may also have enlarged top and bottom ends. The top end of the plug 760 may be configured and shaped to engage the drive shaft 112.

The handle connector 730 may be similarly constructed as handle connector 230, but may be configured and sized differently to accommodate the chamber 740 and the plug 760.

Figure 8:
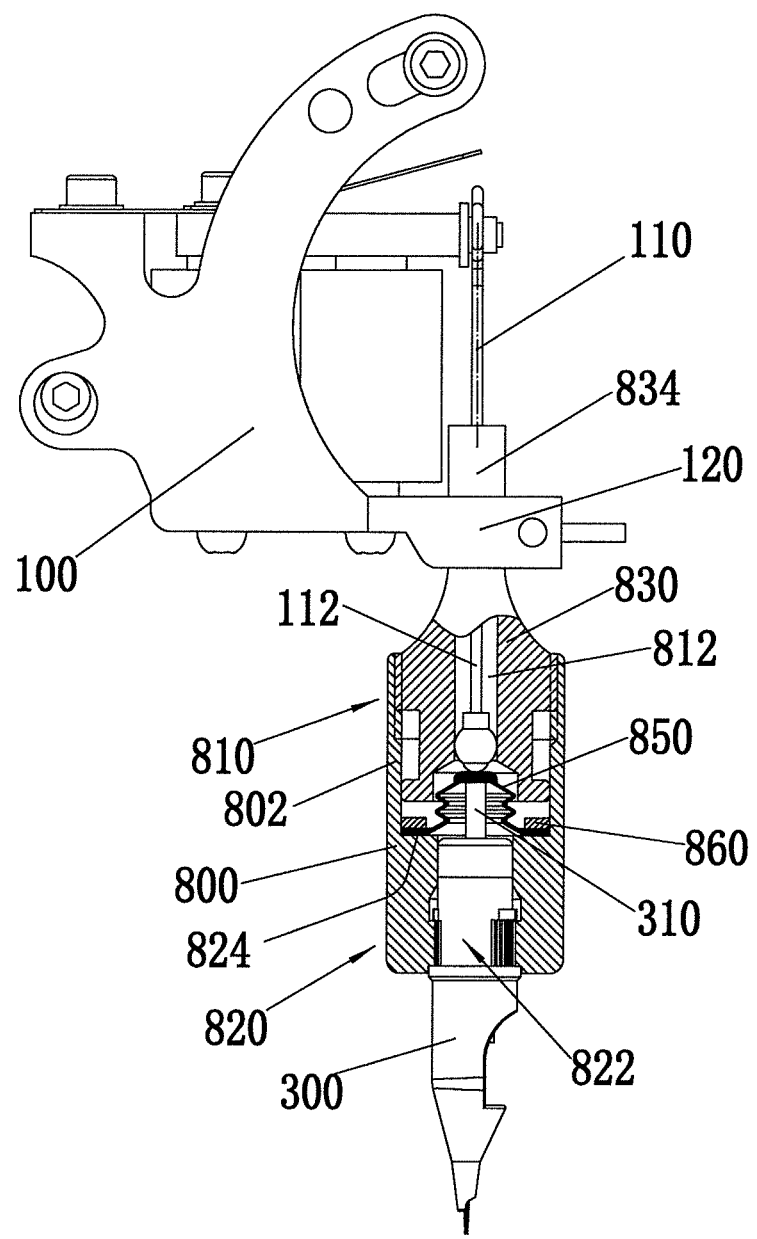
FIG. 8 is a side partial elevation and partial cross-sectional view of another tattooing device, illustrative of another embodiment of the present disclosure.

FIG. 8 illustrates a further embodiment, where the base 100 and needle actuator 110 and the needle module 300 may be as described above. A needle handle 800 including a top portion 810 and a bottom portion 820 is provided.

The top portion 810 is configured for engaging the needle actuator 110 and has an opening 812 for receiving the drive shaft 112 of the needle actuator 110. The top portion 810 may include a connection section 830, which may be integrated with the handle 800 or form a part of the handle 800. Connection portion 830 may be made of a plastic material. Connection portion 830 may be engaged with the tubular wall 802 of the handle 800 by a threaded engagement, or may be affixed to the tubular wall 802 with an adhesive, or by welding such as ultrasonic welding. The top end 834 of the connection portion 830 is shaped and sized to be clamped by the clamp 120 of the base 100.

The bottom portion 820 is configured for engaging the needle module 300 and has an opening 822 for receiving needle shaft 310. A reciprocally movable interface 850 is sealingly affixed to an internal surface in the handle 800.

The interface 850 abuts both drive shaft 112 and needle shaft 310 during operation to allow the needle shaft 310 be indirectly driven by drive shaft 112 through interface 850, and seals and separates the opening 822 in the bottom portion 820 from the opening 812 in the top portion 740. The interface 850 may be formed of a soft or resilient material and may be affixed or mounted inside the handle 800 by any suitable mechanism such as described above.

In an embodiment as depicted in FIG. 8, the bottom opening 822 and top opening 812 may be sized differently so that the openings 812 and 822 form a shoulder 824, and interface 850 may include a sealing cap affixed to the shoulder 824, such as by a constriction ring 860. Alternatively, the sealing cap may be affixed to the shoulder 824 by an adhesive or another suitable affixing technique.

The interface 850 is in contact with the top end of the needle shaft 310 but is not in contact with other parts of the needle module 300. Thus, replacing needle module 300 during use would not damage the interface 850 and would not break the seal between the top and bottom openings 812, 822.

Figure 9:
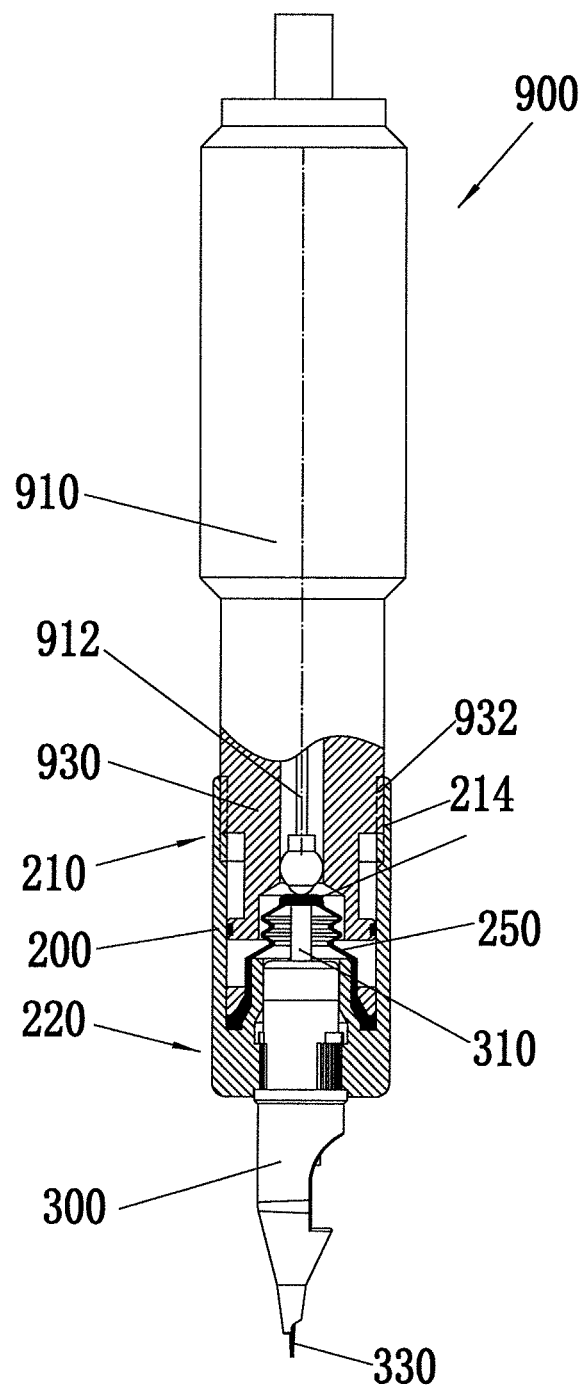
FIG. 9 is a side partial elevation and partial cross-sectional view of a further embodiment of the present disclosure.

FIG. 9 illustrates an embodiment of a tattooing device 900 where the base 910 is configured to connect and engage the handle 200 directly. That is, a connector portion 930 is integrated into the base 910. The connector portion 930 of the base 910 includes a threaded tubular section 932 for engaging the threaded top end 214 of the handle 200. Like base 100, the base 910 also has a needle actuator with a drive shaft 912 for actuating the needle 330 indirectly through the sealing cap 250.

Figure 10A:
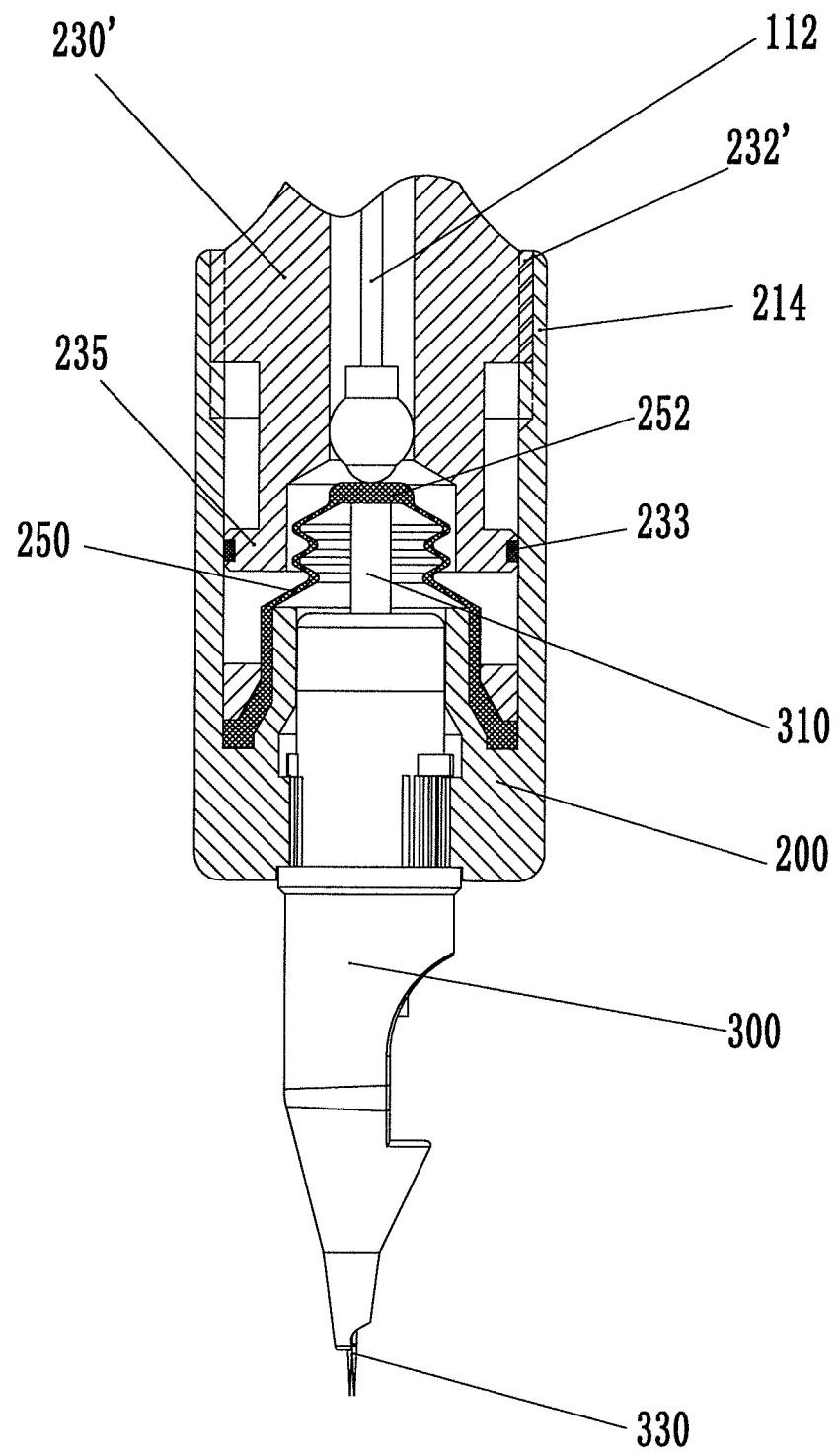
FIGS. 10A and 10B are side partial elevation and partial cross-sectional views of a portion of the tattooing device of FIG. 1, with the needle at different positions during operation.
Figure 10B:
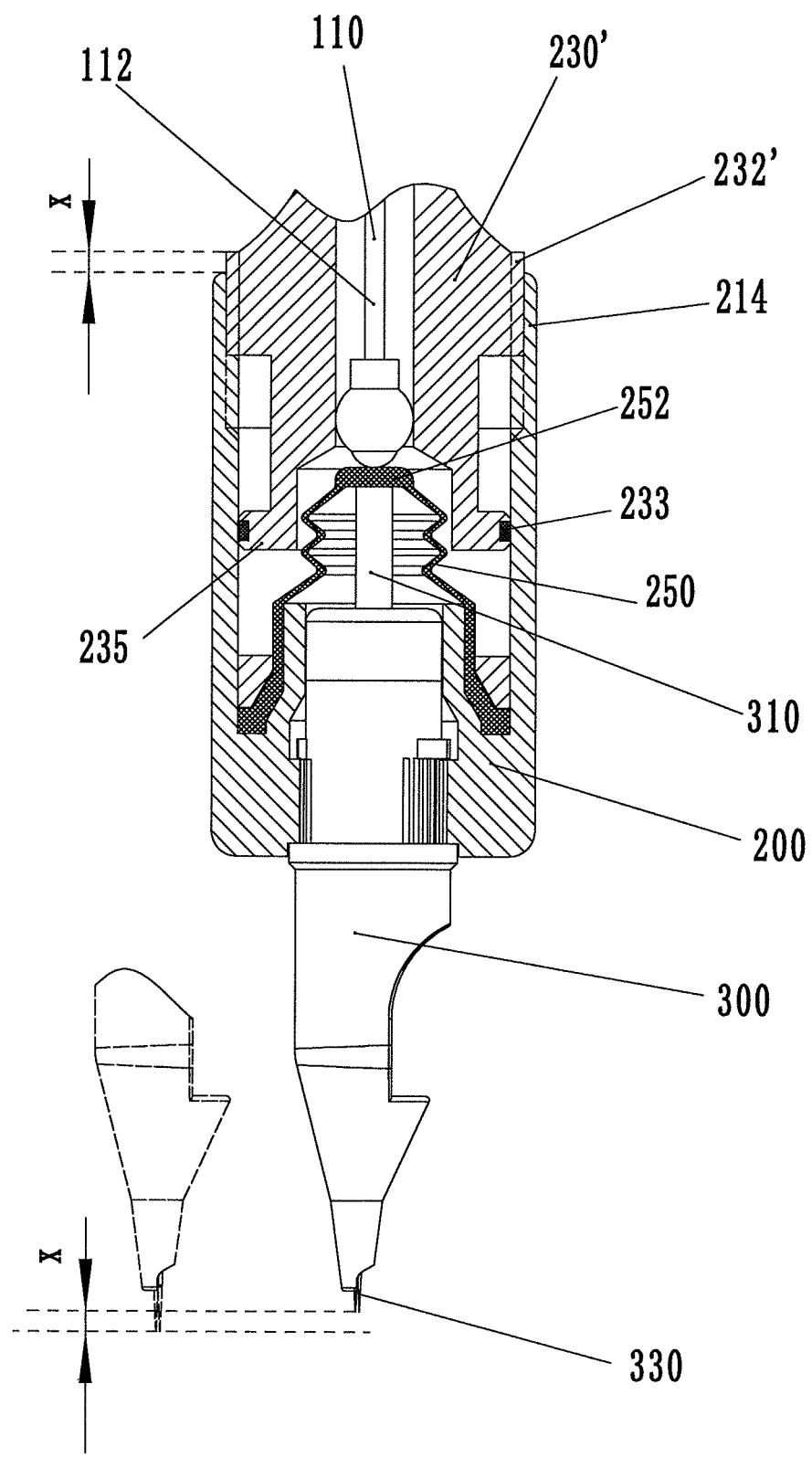

FIGS. 10A and 10B illustrate possible adjustment of the normal needle position in a tattooing device with the handle 200 and a handle connector 230', which is similar but differs from the handle connector 230 as will be described below.

As can be appreciated, adjustment of the normal needle positions may be desirable as different subjects may have different skin thickness and different parts of the same subject may have different skin thickness. Further, there may be other technical or artistic reasons to apply ink or materials to different depths in the skin.

The maximum exposed length of the needle 330 outside the needle module 300 may be adjusted by turning the handle 200 relative to the handle connector 230', which is possible due to the threaded connection at the top end of the handle 200. For example, as illustrated in FIG. 10A, the top ends of the threaded section 214 of the handle 200 and a threaded section 232' of the handle connector 230' are flush. In comparison, the top ends of these threaded sections of the handle 200 and the handle connector 230' are offset in FIG. 10B, by a distance "X". Correspondingly, the exposed length of the needle 330 is longer in FIG. 10A than in FIG. 10B, by a corresponding distance "X", assuming the relative position between the handle connector 230 and the actuator 110 of base 100 (not shown) and the driving shaft 112 has not changed. As the relative position between the handle connector 230' and the handle 200 is changed, the position of the cap top 252 of the sealing cap 250 is also axially adjusted. For example, as the handle connector 230' and drive shaft 112 are moved up as depicted in FIG. 10B, the cap top 252 also moves up due to the resiliency of the sealing cap 250 and a biasing force in the needle module 300 which pushes the needle shaft 310 upwards.

In different embodiments, to adjust the maximum exposed length of the needle 330, it is also possible to adjust the relative axial position of the handle connector 230' with regard to the actuator 110 as discussed above with regard to handle connector 230. When the relative position of the handle connector 230' with regard to the drive shaft 112 is axially adjusted, the maximum exposed length of the needle 330 is also correspondingly extended or shortened, without having to turn the handle 200 relative to the handle connector 230'.

To avoid unintended loosening or turning at the threaded connection between the handle 200 and the handle connector 230', a friction ring 233 may be provided between an enlarged portion 235 of the handle connector 230' and the inner wall of the handle 200. The friction ring 233 may be formed of a rubber, and may provide friction to resist unintended turning of the handle 200 relative to the handle connector 230'. However, the friction ring 233 is configured and sized such that when the operator intentionally turns the handle 200 against the handle connector 230' with an applied torque, the handle 200 can be manually turned relative to the handle connector 230'. In some embodiments, the inner surface of the handle 200 that is in contact with the friction ring 233 may be roughened or rugged to provide additional friction.

As depicted in FIG. 9, the handle connector portion 930 may have similar engagement structures as the handle connector 230' in FIGS. 10A and 10B. It may be appreciated that when the handle connector portion 930 is rotated relative to the handle 200, the base 910 is also rotated and moves up and down with the handle connector portion 930 with respect to the handle 200.

Figure 11:
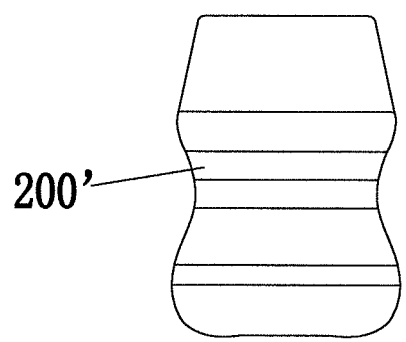
FIG. 11 is a side cross-sectional view of another embodiment of the present disclosure.

FIG. 11 illustrates an handle 200', which differs from the handle 200 in that the tubular shape of the handle 200' is not cylindrical but has a generally vase-shape, and has been sized and shaped to fit comfortably into a hand.

The grip portion of the handle 200' may be ergonomically shaped, and may be deformable so it conforms better to a human hand. Such an ergonomically shaped handle may be more comfortable to use, and may provide health benefits. As can be appreciated, the handle may be provided in different sizes and shapes to fit with different hands, or to conform to different holding habits of different operators.

Figure 12:
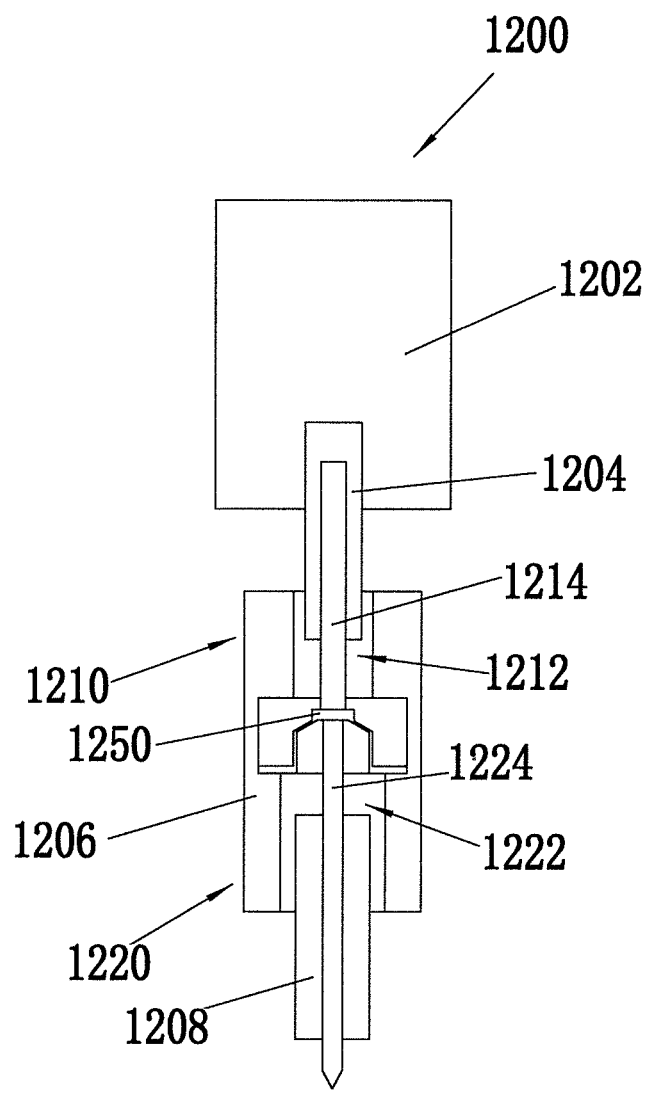
FIG. 12 is a schematic side view of a device for applying coloured liquid to skin, illustrative of a further embodiment of the present disclosure.

FIG. 12 illustrates a further embodiment, a tattooing device 1200, which includes a base 1202 with a needle actuator 1204, a needle handle 1206 removably connected to the base 1202, and a needle module 1208 removably engaged with the needle handle 1206.

The base 1202 may be constructed as the base 100 or as base 910 with needle actuator 1204 constructed as needle actuator 110, and the needle module 1208 may be as constructed as needle module 300.

The needle handle 1206 includes a top portion 1210 and a bottom portion 1220.

The top portion 1210 is configured for engaging the needle actuator 1204 on the base 1202 and has an opening 1212 for receiving a drive shaft 1214 of the needle actuator 1204. The bottom portion 1220 is configured for engaging the needle module 1208 and has an opening 1222 for receiving a needle shaft 1224. A reciprocally movable interface 1250 is sealingly affixed to an internal surface in the handle 1206. The interface 1250 abuts both drive shaft 1214 and needle shaft 1224 during operation to allow the needle shaft 1224 be indirectly driven by the drive shaft 1214 through interface 1250, and seals and separates the opening 1222 in the bottom portion 1220 from the opening 1212 in the top portion 1210. The interface 1250 may be formed of a soft or resilient material and maybe affixed or mounted inside the handle by any suitable mechanism such as described above. The interface 1250 is in contact with the top end of the needle shaft 1224 but is not in contact with other parts of the needle module 1208. Thus, replacing needle module 1208 during use would not damage the interface 1250 and would not break the seal between the top opening 1212 and the bottom opening 1222.

Figure 13:
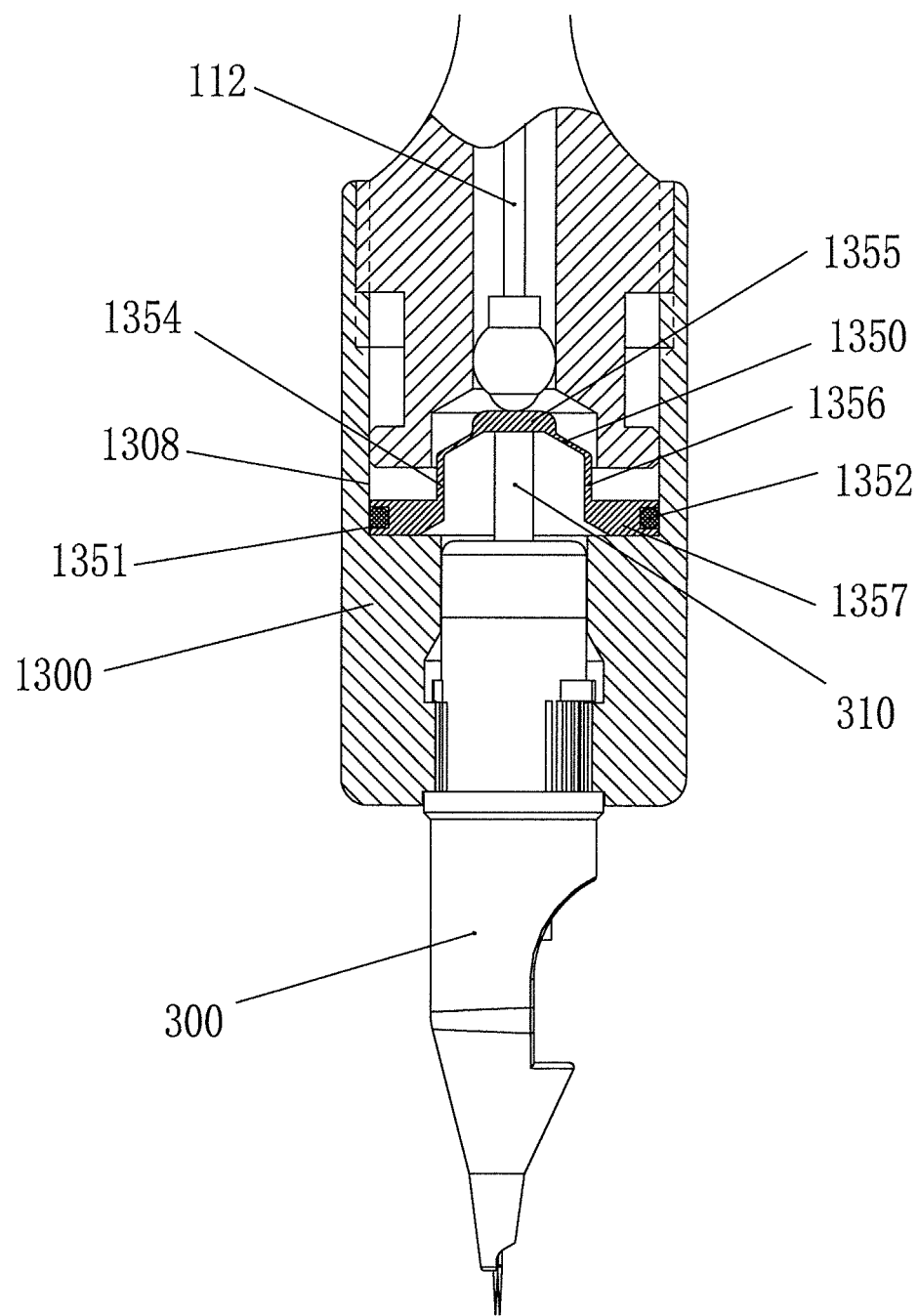
FIG. 13 is a partial cross-section view of a tattooing device, illustrative of another embodiment of the present disclosure.

FIG. 13 illustrates another variation of an embodiment of the handle for a tattooing device. As illustrated in FIG. 13, the interface may be sealingly engaging an internal surface of the handle without being permanently affixed to the surface. For example, the engagement may be a sliding engagement. Specifically, as illustrated, a needle handle 1300 may include an interface 1350, which may include a top portion 1355, middle portion 1356, and bottom portion 1357. Middle portion 1356 connects top and bottom portions 1355, 1357. The bottom portion 1357 has a groove 1351 for a sealing ring 1352. Sealing ring 1352 sealingly engages the internal surface of the handle 1300 when the interface 1350 moves up and down during operation. Sealing ring and bottom portion 1357 may also moves up and down during operation without breaking the seal. Sealing ring 1353 may be an O-ring, and may be made of silicone or rubber. The body 1354 of interface 1350 may be made of a plastic material. Optionally, body 1354 of interface 1350 may be made of rigid silicone with a relatively high hardness. Optionally, in a different embodiment, the sealing ring may be an integral part of the interface body. The middle portion 1356 may be an extendable portion or section, and may include a resilient material or a bellows section. When the middle portion 1356 is extendable and retractable, the axial distance between the top portion 1355 and the bottom portion 1357 can change, allowing more axial movement of the top portion 1355 as compared to the movement of the bottom portion 1357.

As can be appreciated, various modifications may be made to the example devices illustrated in the drawings. For example, the tubular stub 240 and sealing cap 250 may be replaced with a unitary insert which can be a bellows tubing with a closed top end.

The handle and handle connector may be further covered with an external cover to prevent cross contamination during use. The external cover may be formed of a plastic sheet.

The entire tattooing device may also be covered with the external cover during use. It can now be appreciated by those skilled in the art that the devices and applicators disclosed herein provides a needle handle that can be a single-use handle. It is not necessary to clean, sanitize, sterilize, or disinfect the handle immediately prior to use, and the handle can be disposed after a single use without cleaning or other treatment. Thus, the handle is convenient to use.

Other features, modifications, and applications of the embodiments described here may be understood by those skilled in the art in view of the disclosure herein.

CONCLUDING REMARKS

It will be understood that any range of values herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Of course, the above described embodiments of the present disclosure are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A handle for an applicator of a coloured liquid to skin, wherein the applicator comprises a removable needle module and a needle actuator, the needle module comprising a needle, the handle comprising:
a handle body having a top portion and a bottom portion, the top portion engagable with the needle actuator and having a top opening for receiving a drive shaft of the needle actuator, the bottom portion removably engagable with the needle module comprising the needle and the bottom portion having a bottom opening for receiving a needle shaft of the needle; and
a reciprocally movable interface mounted inside the handle body on an internal surface of the handle body between the top opening and the bottom opening and providing a seal between the top portion and the bottom portion, the interface separating the bottom opening from the top opening so as to prevent fluid communication from the bottom opening to the top opening; and configured to abut the drive shaft and the needle shaft during use to allow the drive shaft to indirectly drive the needle shaft,
wherein the handle body comprises a non-removable bottom surface for directly contacting the needle module without contacting the reciprocally movable interface
wherein the interface comprises an interface top portion, a middle portion, and an interface bottom portion, the middle portion connecting the interface top and interface bottom portions, and wherein the middle portion is extendable and retractable.

2. The handle of claim 1, wherein the interface bottom portion comprises a groove and a sealing ring received in the groove, the sealing ring sealingly engaging the internal surface of the handle body.

3. The handle of claim 2, wherein the sealing ring and the interface bottom portion is reciprocally movable along the internal surface of the handle body.

4. The handle of claim 2, wherein the sealing ring is an O-ring.

5. The handle of claim 2, wherein the sealing ring comprises a silicone or a rubber.

6. The handle of claim 2, wherein the sealing ring is an integral part of the interface.

7. The handle of claim 1, wherein the middle portion comprises a resilient material.

8. The handle of claim 1, wherein the middle portion comprises a bellows section.

9. The handle of claim 1, wherein the handle body comprises a plastic material.

10. The handle of claim 1, wherein the interface comprises a plastic material.

11. The handle of claim 1, wherein the top opening and bottom opening are sized and shaped to form a shoulder.

12. The handle of claim 1, wherein the interface is formed of a silicone or a rubber.

13. A tattooing device comprising:
a base comprising the needle actuator of claim 1; and
the handle of claim 1, the top portion of the handle connected to the base.

14. A package comprising:
the handle according to claim 1, wherein the handle has been sterilized; and
a sterilized packaging enclosing the handle therein for keeping the handle in a sterilized condition.

15. A handle for an applicator of a coloured liquid to skin, wherein the applicator comprises a needle and a needle actuator, the handle comprising:
a handle body having a top portion and a bottom portion, the top portion engagable with the needle actuator and having a top opening for receiving a drive shaft of the needle actuator, the bottom portion engagable with a needle module comprising the needle, and the bottom portion having a bottom opening for receiving a needle shaft of the needle; and
a reciprocally movable interface affixed to an internal surface of the handle body between the top opening and the bottom opening and providing a seal between the top portion and the bottom portion, the interface separating the bottom opening from the top opening so as to prevent fluid communication from the bottom opening to the top opening, and configured to abut the drive shaft and the needle shaft during use to allow the drive shaft to indirectly drive the needle shaft, wherein the handle body comprises a non-removable bottom surface for directly contacting the needle module without contacting the movable interface wherein the interface comprises rises an interface to portion a middle portion and an interface bottom portion, the middle portion connecting the interface top and interface bottom portions, and wherein the middle portion is extendable and retractable.

16. The handle of claim 15, wherein the top opening and bottom opening are sized and shaped to form a shoulder, and the interface comprises a sealing cap affixed to the shoulder.

17. The handle of claim 15, wherein the interface bottom portion comprises a fixed base portion; wherein the interface to portion is a movable top portion; and wherein the middle portion is a bellows portion connecting the interface bottom portion and the interface top portion.

* * * * *

UNITED STATES PATENT AND TRADEMARK OFFICE
CERTIFICATE OF CORRECTION

| | |
|---|---|
| PATENT NO. | : 11,197,986 B2 |
| APPLICATION NO. | : 16/543913 |
| DATED | : December 14, 2021 |
| INVENTOR(S) | : Xiao |

It is certified that error appears in the above-identified patent and that said Letters Patent is hereby corrected as shown below:

In the Claims

Column 13:
Lines 6 and 7, "the interface comprises rises an interface to portion a middle portion and an interface bottom" should be changed to read --"the interface comprises an interface top portion, a middle portion, and an interface bottom--;
Line 16, "to portion is a movable top portion" should be changed to read --top portion is a movable top portion--.

Signed and Sealed this
Third Day of May, 2022

Katherine Kelly Vidal
Katherine Kelly Vidal
*Director of the United States Patent and Trademark Office*